United States Patent
Siedenburg

(10) Patent No.: US 12,279,914 B2
(45) Date of Patent: Apr. 22, 2025

(54) INTERNAL BLEEDING DETECTION, ASSESSMENT AND MONITORING DEVICES, SYSTEMS AND METHODS

(71) Applicant: Stryker Corporation, Kalamazoo, MI (US)

(72) Inventor: Clinton T. Siedenburg, Everett, WA (US)

(73) Assignee: Stryker Corporation, Portage, MI (US)

( * ) Notice: Subject to any disclaimer, the term of this patent is extended or adjusted under 35 U.S.C. 154(b) by 50 days.

(21) Appl. No.: 18/144,788

(22) Filed: May 8, 2023

(65) Prior Publication Data
US 2023/0355217 A1  Nov. 9, 2023

Related U.S. Application Data

(63) Continuation of application No. 16/103,837, filed on Aug. 14, 2018, now Pat. No. 11,642,106.

(60) Provisional application No. 62/545,440, filed on Aug. 14, 2017.

(51) Int. Cl.
*A61B 8/00* (2006.01)
*A61B 8/08* (2006.01)

(52) U.S. Cl.
CPC .......... *A61B 8/56* (2013.01); *A61B 8/08* (2013.01); *A61B 8/085* (2013.01); *A61B 8/4236* (2013.01); *A61B 8/5223* (2013.01); *A61B 8/565* (2013.01); *A61B 8/4483* (2013.01); *A61B 8/54* (2013.01)

(58) Field of Classification Search
CPC .. A61B 8/56; A61B 8/08; A61B 8/085; A61B 8/4236; A61B 8/5223; A61B 8/565; A61B 8/4483; A61B 8/54
See application file for complete search history.

(56) References Cited

U.S. PATENT DOCUMENTS

| | | |
|---|---|---|
| 9,893,538 B1 | 2/2018 | Bell et al. |
| 10,835,207 B2 | 11/2020 | Altmann et al. |
| 2009/0003675 A1 | 1/2009 | Moreau-Gobard |
| 2010/0160781 A1 | 6/2010 | Carter et al. |
| 2010/0268088 A1 | 10/2010 | Prus et al. |
| 2014/0031659 A1* | 1/2014 | Zhao ................ A61B 1/00193 600/371 |
| 2014/0288428 A1 | 9/2014 | Rothberg et al. |

(Continued)

OTHER PUBLICATIONS

Office Action for U.S. Appl. No. 16/103,837, mailed on Mar. 12, 2021, Siedenburg, "Internal Bleeding Detection, Assessment and Monitoring Devices, Systems and Methods", 15 pages.

(Continued)

*Primary Examiner* — Joseph M Santos Rodriguez
*Assistant Examiner* — Zainab Mohammed Aldarraji
(74) *Attorney, Agent, or Firm* — Lee & Hayes, P.C.

(57) ABSTRACT

Internal bleeding systems, devices, and methods are disclosed that include a sensing module and a processing module. The sensing module has an ultrasound module and a communication module. The ultrasound module emits and receives ultrasound energy to and reflected from tissue in a patient and generates a reflected energy signal. The communication module transmits the reflected energy signal to the processing module. The processing module analyzes the reflected energy signal to determine if it indicates the presence of blood from internal bleeding in the patient.

20 Claims, 4 Drawing Sheets

(56) References Cited

U.S. PATENT DOCUMENTS

| | | |
|---|---|---|
| 2014/0378835 A1* | 12/2014 | Satoh .................. A61B 8/0891 |
| | | 600/456 |
| 2015/0201907 A1* | 7/2015 | Stergiopoulos .... A61B 5/02042 |
| | | 600/371 |
| 2016/0089108 A1* | 3/2016 | Kim .................... G01S 7/52066 |
| | | 600/443 |
| 2016/0089117 A1 | 3/2016 | Kim |
| 2016/0317123 A1* | 11/2016 | Kinnon Dahlgren ........................ |
| | | A61B 8/4427 |
| 2017/0105700 A1 | 4/2017 | Bar-Zion et al. |
| 2017/0172545 A1 | 6/2017 | Lee et al. |
| 2017/0258332 A1 | 9/2017 | Wynn et al. |
| 2017/0258445 A1 | 9/2017 | Van Alphen et al. |

OTHER PUBLICATIONS

Office Action for U.S. Appl. No. 16/103,837, mailed on Jul. 23, 2021, Siedenburg, "Internal Bleeding Detection, Assessment and Monitoring Devices, Systems and Methods", 18 pages.

Office Action for U.S. Appl. No. 16/103,837, mailed on Jun. 16, 2022, Siedenburg, "Internal Bleeding Detection, Assessment and Monitoring Devices, Systems and Methods", 26 pages.

* cited by examiner

INTERNAL BLEEDING DETECTION, ASSESSMENT AND MONITORING DEVICES, SYSTEMS AND METHODS

CROSS-REFERENCE TO RELATED APPLICATIONS

This patent application is a continuation of U.S. patent application Ser. No. 16/103,837, filed Aug. 14, 2018, entitled "INTERNAL BLEEDING DETECTION, ASSESSMENT AND MONITORING DEVICES, SYSTEMS AND METHODS," which claims the benefit of and priority to U.S. Provisional Patent Application Ser. No. 62/545,440, filed on Aug. 14, 2017, entitled "NON-INVASIVE DETECTION OF INTERNAL BLEEDING USING ULTRASOUND," the contents of each of which are hereby incorporated by reference in their entirety.

BACKGROUND

Internal bleeding is a loss of blood that occurs within the body and often results in the lost blood pooling, or collecting, within cavities and spaces within the body. The presence of internal bleeding within a patient can present or indicate a critical condition that requires monitoring and/or treatment for the health of the patient. In conventional practice, to determine if there is internal bleeding present in a patient, a diagnostic scan is often performed by a trained medical technician/professional, such as a focused assessment with sonography for trauma (FAST) exam. Before the diagnostic scan can be performed, conventional trauma protocol requires that the patient must usually have a strong indication that such a scan is warranted due to the cost and time of performing the scan. If such an indication is not present, the diagnostic scan may be declined. The patient may still be suffering internal bleeding even without strong indicators required by the conventional protocol or internal bleeding may be imminent in the patient but not yet presenting with strong indicators required by the protocol. This can result in the patient having internal bleeding that is not detected until reaching a later, more clinically significant state, which can have an adverse impact on the health and/or outcome of the patient.

Internal bleeding detection, assessment and/or monitoring can be improved by non-invasive devices, systems and methods that cost less, improve treatment outcomes, increase accuracy of detecting internal bleeding, and decrease the amount of time to detect internal bleeding, such as for the purposes of monitoring and/or treating the patient.

DETAILED DESCRIPTION

Figure 1:
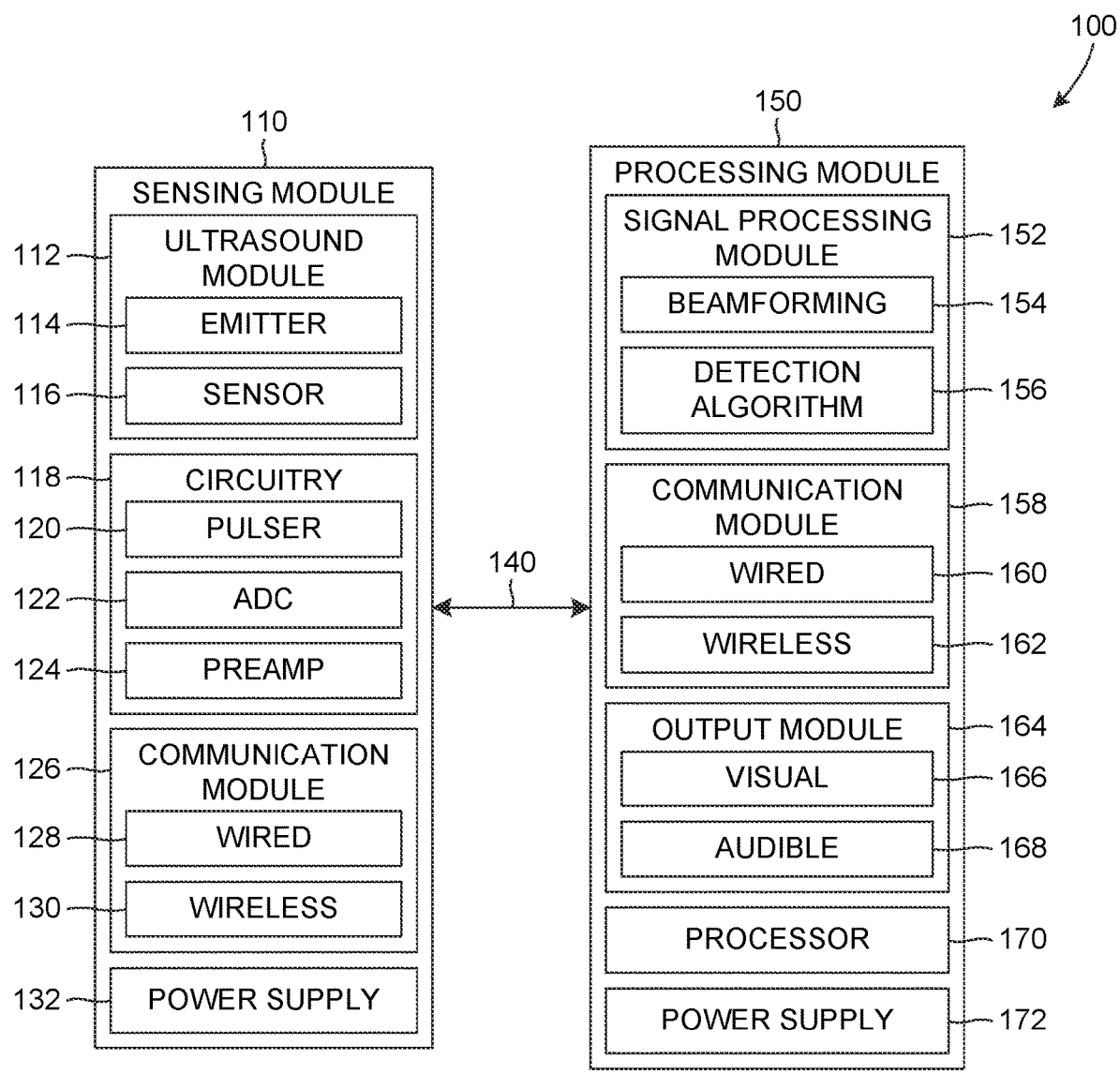
FIG. 1 is an example internal bleeding detection and/or assessment system.

The disclosed devices, systems and methods non-invasively detect, assess and/or monitor internal bleeding within a patient. Conventional emergency and trauma protocol requires a medical professional to have a strong indicator that the patient is suffering internal bleeding. The treatment is a FAST exam, which typically includes an ultrasound diagnostic exam of the patient's condition to detect internal bleeding. Many patients have internal bleeding without strong indicators and other patients are imminently about to start suffering internal bleeding that goes undetected for a period of time. The disclosed devices, systems and methods can detect internal bleeding in patients that do not qualify for the FAST exam and/or that need ongoing monitoring to detect trends in known internal bleeding or commencement of internal bleeding in a patient at risk for such condition. The disclosed devices, systems, and methods use a low channel count, ultrasound acquisition technique to interrogate a volume of interest in the patient, likely one of the common areas that are examined for free fluid in patients at risk for internal bleeding—the perihepatic space, the perisplenic space, the pericardium and the pelvis, for example.

Conventional ultrasound systems interrogate tissue of interest using a generally high channel count relative to the number of ultrasound transducers in the systems (typically at least 1 channel to 4 transducers) to produce high resolution images for monitoring and diagnostic purposes. The disclosed devices, systems, and methods instead have a low channel count relative to the number of ultrasound transducers, which results in a slower imaging rate. The slower imaging rate of interrogating volumes of interest for internal bleeding can be afforded due to the relatively slow growth of a pool of blood. The output of the disclosed devices, systems, and methods does not require, although it could include, an image. The output includes an indicator that alerts a user or rescuer that a pool of blood is present or is growing. The indicator can be audible and/or visual and can be arranged for quick reads by a user, such as a light, yes/no audible or visual output, or other non-image output. An image can also be included, if desired, with the non-image indicator.

Ultrasound energy is emitted into the patient tissues and a reflected energy signal is generated based on the ultrasound energy reflected from the patient tissues. The reflected energy signal can be processed to divide the volume of patient tissues interrogated by the ultrasound energy into individual volumes, or voxels. The reflected energy power level of the individual volumes can be compared to a threshold value(s), or range(s), to determine if the individual volume indicated the presence of blood, such as can be caused by internal bleeding. The individual volumes indicating the presence of blood can be quantified, such as a number or volume thereof. The quantification can cause an alarm to be output. Additionally, the quantification can be compared to previous quantifications to assess/monitor the change, and/or rate of change, of internal bleeding within the patient.

FIG. 1 illustrates an example internal bleeding detection and/or assessment system 100. The system 100 includes a sensing module 110 that is placed on a patient to transmit ultrasound energy into the tissues of the patient and to receive reflected ultrasound energy from the tissues. The sensing module 110 relays, or communicates, the received reflected energy, or a signal/data generated in response to receiving the reflected energy, to a processing module 150. The received reflected energy signal/data is processed by the processing module 150 to determine the presence of internal bleeding, to quantify internal bleeding and/or monitor internal bleeding within the patient. Based on the detection and/or monitoring of internal bleeding, the processing module 150 can output an alert to notify a user, device and/or system of the presence of internal bleeding within the patient and/or characteristics of the internal bleeding, such as an increasing volume of the internal blood pool.

The sensing module 110 includes an ultrasound module 112, circuitry 118, a communication module 126 and a power supply 132 to emit ultrasound energy, received reflected ultrasound energy and transmit the reflected energy signal/data to the processing module 150. The sensing module 110 can be a physical device, or included in a device, that is placed on a patient to acquire, or obtain, the reflected energy signal. During use, the sensing module 110 can remain placed on the patient to allow for extended monitoring of the patient, such as to detect or monitor internal bleeding within the patient. In an example, the sensing module 110 can be integrated into a patch that can be placed on, or affixed to, the patient to detect for, or monitor, internal bleeding within the patient. The patch can be disposable in some examples or alternatively reusable. Acquisition, and/or transmission, of the reflected energy signal can be in a continuous, regular, or sporadic manner, and can be optionally controlled by the processing module 150, which can be done by an integrated or separate control module, for example.

The ultrasound module 112 includes an emitter 114 to generate and emit ultrasound energy and a sensor 116 for receiving the reflected ultrasound energy. The emitter 114 and sensor 116 can be integrated into a single transducer element that can both emit and sense ultrasound energy. The emitter 114 emits ultrasound energy that is transmitted into tissues of the patient. The ultrasound energy transmits through the tissues and reflects from the tissues, structures and/or features therein. The higher reflectivity features of, or within, the tissues reflect more ultrasound energy than those having less reflectivity, such as fluids within the tissues. The reflected ultrasound energy is received by the sensor 116 and causes the sensor 116 to generate a signal/data indicative of, or in response to, the received reflected ultrasound energy. The reflected energy signal/data can then be communicated to the processing module 150 by the communication module 126.

Multiple emitters 114 and sensors 116, or transducers, can be included in the ultrasound module 112. The multiple emitters 114 and sensors 116, or transducers, can be arranged in various formations, such as an array, to emit and sense ultrasound energy. Additionally, one or more of the emitters 114 can be individually selected or selected as a group of emitters 114, to emit ultrasound energy. In this manner, one or more emitters 114 can be sequentially activated to emit ultrasound energy, which can allow for a requisite, or desired, interrogation of the patient's tissues using the ultrasound energy.

The circuitry 118 can connect to each of the emitters 114 and sensors 116, or transducers, to assist with emission and reception of ultrasound energy. The circuitry 118 can include a pulser 120, and analog-to-digital converter (ADC) 122 and a preamp 124. The various elements of the circuitry 118 can be individually connected to each of the emitters 114 and sensors 116, or transducers, or connected to groups of emitters 114 and sensors 116, or transducers.

The pulser(s) 120 are electrically coupled to and can supply energy to the emitters 114 to cause the emitters 114 to generate and emit ultrasound energy. The pulser 120 can supply the energy at a power level to cause the ultrasound energy emitted by the emitters 114 to have a desired, or required, power level. Additionally, the pulser 120 can repeatedly activate the emitters 114 at varying power levels to vary the depth of tissue to which the ultrasound energy is transmitted and reflected. For example, the pulser 120 can be set to a tissue penetration depth of which all shallower depths of interest are in view and processed. The tissue penetration depth can be set by the power level. Further, the energy supplied by the pulser 120 can be a signal having various signal characteristics, such as a waveform, amplitude, frequency and/or wavelength, which can cause the ultrasound energy emitted by the emitters 114 to have desired, or required, signal characteristics. For example, the pulser 120 can cause the emitters 114 to emit ultrasound energy in a concerted manner, such as in the form of a plane wave. As discussed above, the pulser 120 can be connected to each emitter 114, or transducer, individually which can allow for the selective activation of one or more emitters 114 to emit ultrasound energy into the patient tissues.

The ADC 122 and preamp 124 can be connected to the sensors 116, or transducers. The preamp 124 can amplify, and/or optionally filter, for example to improve signal to noise ratio, the reflected energy signal output by the sensors 116, or transducers, and the ADC 122 can digitize the amplified and/or filtered reflected energy signal in preparation for communication to the processing module 150. In an example embodiment, sampling rate of the ADC 122 can be selected, or set, based on the available communication bandwidth for transmission of the reflected energy signal to the processing module 150.

Additional signal processing hardware and/or software can be included in the circuitry 118 to further process the reflected energy signal/data before communication to the processing module 150. For example, additional signal processing can include reducing the noise bandwidth of and/or base-banding the reflected energy signal/data to assist with the communication, or transmission, of the reflected energy signal/data to the processing module 150.

The communication module 126 communicates 140 with the processing module 150 to transmit and receive data there between. The reflected energy signal/data from the ultrasound energy module 112 and circuitry 118 is provided to the communication module 126 for transmission to the processing module 150. Communication between the communication module 126 and processing module 150 can be in a continuous or interval manner, and can be initiated, and/or controlled, by the sensing module 110 and/or the processing module 150. A control module can control this communication either as a separate or integrated component.

The communication module 126 can include wired 128 and/or wireless 130 connections, systems and/or protocols. The wired connection 128 can include a physical connection connecting the sensing module 110 to the processing module 150 to transmit data, such as the reflected energy signal. The wireless connection 130 can include one or more wireless communication elements, devices and/or systems that can use one or more wireless communication methods and/or protocols. Example wireless connections 130 can include a local area (LAN), wide area (WAN), ad-hoc, Bluetooth Wi-Fi, Wi-Fi Direct, and/or other wireless connections/communications, methods and/or protocols. The wireless connection 126 has sufficient bandwidth to transmit the reflected energy signal/data from the sensing module 110 to the processing module 150.

The power supply 132 can be an integrated, permanent, replaceable, rechargeable, and/or external power source that provides power, such as electrical power, to the various functions and/or features of the sensing module 110. In an example, the power supply 132 can be an energy storage device, such as a battery, that supplies the requisite or desired power to the functions/features of the sensing module 110. In another example, power can be supplied by the processing module 150 to the sensing module 110 through a physical or wireless connection, such as by a wired or an inductive coupling.

In an alternative embodiment, the power supply 132 can include energy harvesting capabilities/features to allow for the harvesting of ambient energy about the sensing module 110 to provide the requisite or desired power to the functions/features of the sensing module 110. Example ambient energy sources can include light, thermal, motion and or electromagnetic energy that can be harvested and provided to the functions and/or features of the sensing module 110.

The processing module 150 includes a signal processing module 152, a communication module 158, an output module 164, a processor 170 and a power supply 172. The processing module 150 receives the reflected energy signal/data from the sensing module 110 and processes the received signal/data to detect, monitor and/or assess internal bleeding within the patient. Monitoring and/or assessing internal bleeding within the patient can include quantifying the internal bleeding and/or monitoring changes to the internal bleeding, such as an increasing volume.

The signal processing module 152 can process the received reflected energy signal/data using beamforming 154 and a detection algorithm 156 to detect, quantify, monitor and/or assess internal bleeding within the patient. The signal processing module 152 can be coupled to or implemented on the processor 170 to assist with processing the received reflected energy signal/data.

The beamforming 154 generates a voxel, which is a three-dimensional volumetric pixel, using the reflected energy signal/data. The voxel generated by the beamforming 154 represents a volume of patient tissues interrogated by ultrasound energy, the reflection from which was received by the sensor 116. In this manner, a set of voxels is generated from the sensors 116, or a group of sensors 116, from the reflected energy signal/data. The beamforming 154 uses the time varying reflected energy signal/data from the sensor(s) 116, applies weights and delays to the reflected energy signal/data to generate the voxel. Multiple voxels are generated by beamforming 154 for the volume of interest, which is the volume being interrogated by the ultrasound module 112 of the sensing module 110. Each of the voxels represents a specific portion of the overall volume of interest and the tissues therein, including blood pools.

The detection algorithm 156 can analyze each of the voxels to determine the presence of blood in each voxel. A power level of each of the voxels can be assessed to determine whether the power level is above or below a threshold value and/or within or outside of a range of threshold values. Free, or pooled, blood within tissues, such as might be caused by internal bleeding, is a fluid and less reflective than many of the tissues that would be around the free blood. Due to the lower reflectivity of the free blood, compared to the reflectivity of the surrounding tissues, the free blood reflects less ultrasound energy, thus resulting in a reflected energy signal of lower power relative to the reflected energy signal from more reflective tissues. The detection algorithm can compare the power level of each voxel to a threshold value(s) to determine the presence of free blood within the volume of tissue represented by the voxel.

The threshold value(s) can be predetermined, generated, editable, and/or inputted value(s) relative to which the power level of each voxel is compared or assessed. In an example embodiment, the detection algorithm can include a predetermined threshold value(s), or range(s). The voxel power level is compared or assessed relative to the presence of free blood in the tissues. The predetermined threshold value(s) can be optionally editable, or adjustable, by a user and/or other device/system, such as a trained medical professional. Adjusting the threshold value(s) can alter the sensitivity and/or accuracy of detecting, assessing and/or monitoring the presence of free blood in the tissues. In another example embodiment, the threshold value(s) can be generated by the detection algorithm 156 based on the relative power of the voxels. For example, the processing module 150 can automatically determine power level(s), or ranges, to associate with tissues within the volume of interest and can base a threshold value(s) for the voxel power level based on this determination, or vice versa. In another example embodiment, power level of a voxel can be compared to the power level of surrounding, or other, voxels. The difference in power levels of the voxels can be indicative of the voxels representing the same, or similar, tissues or representing differing tissues. Using this comparison, the detection algorithm 156 can effectively map the various tissues and fluids within the volume of interest and associate appropriate threshold value(s) based on the relative comparison.

In addition to assessing the power level of the voxels to determine the presence of free blood, the detection algorithm 156 can also quantify the number of voxels having the presence of free blood, quantify the volume of free blood and/or monitor the free blood. To quantify the number of voxels, the detection algorithm 156 can calculate the number of voxels that do not exceed, or are within, the threshold value(s). Additionally, the detection algorithm 156 can provide a ratio of the voxels that indicate the presence of free blood, those that do not exceed the threshold value(s), to the voxels that do not indicate the presence of free blood. To quantify the volume of free blood, the algorithm 156 can use the quantification of the voxels indicating the presence of blood with the volumetric measurement of each of the voxels to provide a measurement of the volume of free blood within the volume of interest.

To monitor the presence of free blood, the detection algorithm 156 can repeatedly assess, or detect the presence of free blood in the volume of interest and compare to previous assessments/detections. In this manner, the detection algorithm 156 can determine whether a volume of free blood is changing and/or present. The detection algorithm 156 can provide an assessment and/or measurement of the changes in the volume of free blood and can also include a threshold value(s) of a volume of free blood, or rate of change in the volume of free blood, that causes an alert to be issued by the processing module 150, such as by the output module 164. Multiple alert threshold value(s) can be included and associated with varying degrees of alert to be output.

The communication module 158 of the processing module 150 can include one or more wired 160 and/or wireless connections 162. The communication module 158 can operate similarly to the communication module 126 of the sensing module 110 and can assist with communication between the sensing module 110 and processing module 150. Additionally, the communication module 158 can communicate with another external device and/or system, such as a patient monitoring device/system, to provide information and/or data, such as an indication of the presence, or an assessment, of internal bleeding within the patient.

The output module 164 can include a visual 166 and/or an audible output 168 to provide an output, such as a presence or an assessment of internal bleeding within the patient and/or information regarding the processing module 150, such as a status. Additionally, the output module 164 can output an alarm, notification, and/or indication of the presence of internal bleeding and/or the internal bleeding exceeding a threshold value, such as a volume or rate of change. Example visual outputs 166 can include a screen, lights, indicators, and/or other visual outputs that provide a visual indication of the processing module 150. Example audible outputs 168 can include a speaker, buzzer, annunciator, and/or other audible output that provides an audible indication of the processing module 150.

The processor 170 can be coupled to one or more elements of the processing module 150 to assist with, and/or control the various operations, functions and/or features of the processing module 150. In an example, the processor 170 can be coupled to the signal processing module 152 to assist with, or perform, the beamforming 154 and/or execute the detection algorithm 156.

The power supply 172 may be an integrated, permanent, replaceable, rechargeable, and/or external power source that provides power, such as electrical power, to the various functions and/or features of the processing module 150. In an example, the power supply 172 can be an energy storage device, such as a battery, that supplies the requisite or desired power to the functions/features of the processing module 150. Additionally, the power supply 172 can be coupled to the sensing module 110 to provide power to it. The coupling can be a physical connection, such as a wire, and/or a wireless connection, such as an inductive power coupling.

Figure 2:
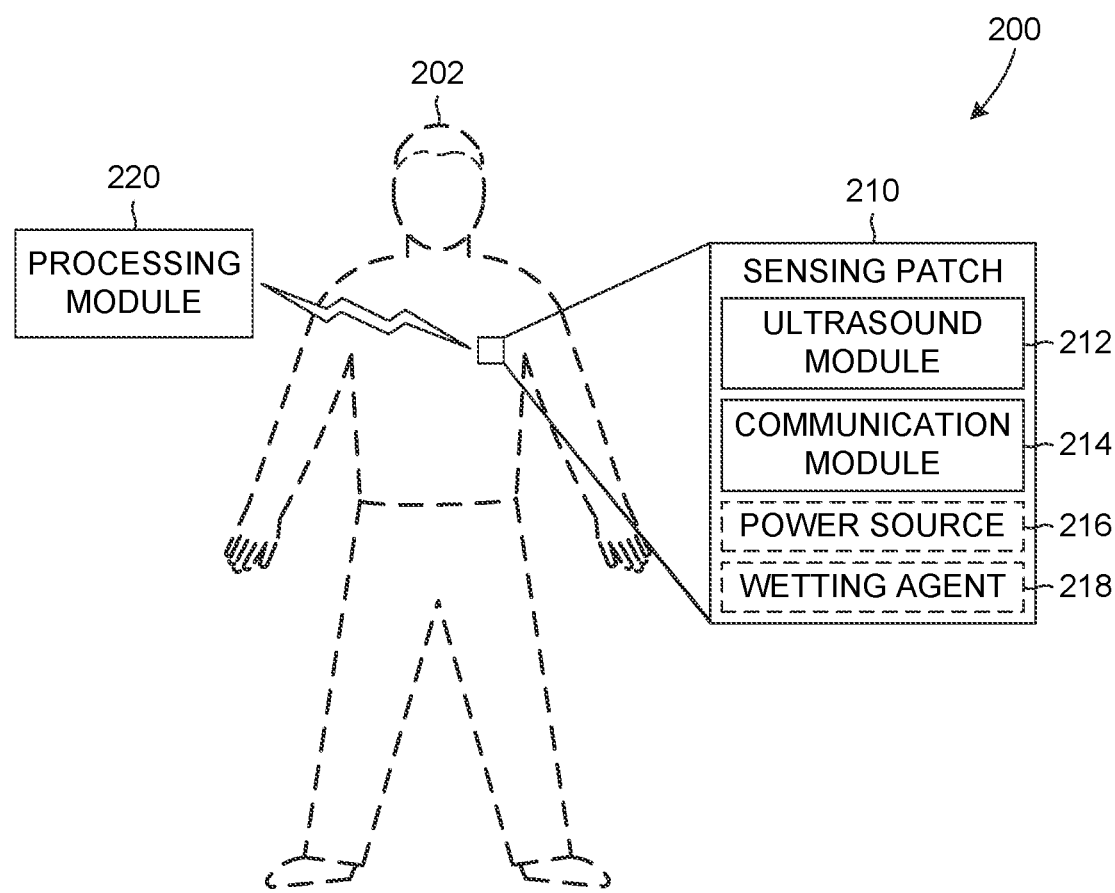
FIG. 2 is a further example internal bleeding detection, assessment and/or monitoring system.

FIG. 2 illustrates an example internal bleeding detection, assessment and/or monitoring system 200. The system 200 includes a sensing patch 210 that can be placed on, or affixed to, a patient 202. The sensing patch 210 can transmit data, such as a reflected energy signal, to the processing module 220 which can detect, assess and/or monitor internal bleeding within the patient 202. While a single sensing patch 210 is shown on the patient 202, multiple sensing patches 210 can be distributed across the patient 202 to provide for internal bleeding detection, assessment and/or monitoring of the patient, or specific target areas. For example, the sensing patches 210 can be placed at one or more of the four common areas for blood to pool if a patient is suffering internal bleeding: the perihepatic space, the perisplenic space, the pericardium, and the pelvis. Other areas of the patient may additionally or alternatively be monitored as well. Multiple patches could be placed at a single or multiple area(s) of concern as well.

The sensing patch 210 includes an ultrasound module 212 and a communication module 214, and, optionally, a power source 216 and/or wetting agent 218. The ultrasound module 212 emits ultrasound energy into tissues of the patient 202 and receives reflected ultrasound energy from those tissues. The reflected energy generates a reflected energy signal, or data, that can be transmitted to the processing module 220 for processing.

The ultrasound module 212 can include one or more transducers for emitting and receiving ultrasound energy. The transducers of the ultrasound module 212 can be arranged, such as in an array, to emit ultrasound energy into the tissues in a desired, or required, manner. The emitted ultrasound energy reflects from the patient 202 tissues, such as free blood present in it. The reflected ultrasound energy is received by the transducers of the ultrasound module 212 and causes the reflected energy signal be generated. The ultrasound module 212 can also include various circuitry, such as a pulser, analog-to-digital converter (ADC) and/or preamp, to assist with the emission of ultrasound energy and/or sampling/processing the received reflected energy signal/data.

The communication module 214 can communicate with the processing module 220 to transmit data from the sensing patch 210, such as the reflected energy signal/data, and/or receive data to the sensing patch 210, such as operation commands. The communication module 214 can use a wired and/or a wireless connection between the processing module 220 and the sensing patch 210 for communication. Various wireless communication devices, protocols and/or methods can be used to communicate between the sensing patch 210 and processing module 220.

The optional power source 216 can be an integrated, permanent, replaceable, rechargeable, and/or external power source that provides power, such as electrical power, to the various functions and/or features of the sensing patch 210. In an example, the power source 216 can be an energy storage device, such as a battery, that supplies the requisite or desired power to the functions/features of the sensing patch 210. In another example, power can be supplied by the processing module 220 to the sensing patch 210 through an inductive coupling. Alternatively, or additionally, the power source 216 can include energy harvesting capabilities to harvest ambient energy, such as thermal, light and/or electromagnetic energy, from the environment about the sensing patch 210 and provide the harvested energy to the various functions and/or features of the sensing patch 210.

The sensing patch 210 can also include an optional wetting agent 216 to facilitate the transmission/reception of the ultrasonic energy into the patient 202 tissues. The sensing patch 210 can have a self-dispensing wetting agent that is applied to the patch and/or the patient before, while, or after the patch is placed on, or applied. For example, placing the sensing patch 210 on the patient 202, or as part of such action, can cause the wetting agent 216 to be released beneath the ultrasound module 212 to assist with transmission of the emitted energy into the tissues of the patient 202 and/or reception of reflected energy from the tissues. Alternatively, a user can separately apply the wetting agent to the patch and/or patient before the emission of energy begins.

The sensing patch 210 can be a disposable or reusable article that is applied to the patient 202 to detect, assess and/or monitor internal bleeding within the patient 202. In an example, the patient 202 can experience an injury or trauma requiring treatment at a medical facility and/or by a medical professional. One or more sensing patches 210 can be placed on the patient 202, such as around a location of the injury, at common locations at which internal bleeding typically pools or collects, and/or locations where internal bleeding detection/assessment can be critical/impactful to the physiological state of the patient. These sensing patches 210 can be placed onto, and remain on, the patient 202 as the patient 202 undergoes various monitoring and treatment for the injury. Continuous and/or periodic monitoring of signals and/or data generated by the sensing patches 210 can be performed to detect, assess and/or monitor internal bleeding within the patient 202. Various monitoring and treatment decisions regarding the patient 202 can be made based on, and/or assisted by, the internal bleeding information provided by the internal bleeding detection, assessment and/or monitoring system 200.

The processing module 220 receives the reflected energy signal/data from the sensing patch 210 and processes the reflected energy signal/data to detect, assess and/or monitor internal bleeding within the patient 202. The processing module 220 can use beamforming to generate one or more voxels, three-dimensional, volumetric pixels, from the reflected energy signal/data. A detection algorithm of the processing module 220 can assess each of the voxels for an indication, or presence, of blood, such as a result of internal bleeding, by comparing a power level of each voxel to a threshold value(s) and/or threshold range(s). The threshold value(s)/range(s) can be computed relative to other tissues, predetermined, preselected, adjustable and/or input by the processing module 220, a user, and/or external device/system. The detection algorithm can also indicate the presence and/or assessment of internal bleeding within the patient 202 by quantifying the voxels indicating the presence of internal bleeding, such as providing a number of voxels that are below the threshold value(s) or within the range(s), providing a ratio of voxels that are below the threshold value(s) or within the range(s) to the total number of voxels or those not below the threshold value(s) or within the range(s), and/or a measuring a volume (or other unit(s)) of the voxels that are below the threshold value(s) or within the range(s). Additionally, the detection algorithm can compare present internal bleeding data to previously acquired internal bleeding data to assess and/or monitor changes in the internal bleeding of the patient 202, such as a change in the rate of change of the internal bleeding and/or change in the volume of the internal bleeding.

The results of the detection algorithm can be output by the processing module, such as by a visual and/or audible output, and/or can be transmitted to a user and/or external device/system. Additionally, the detection algorithm can include additional threshold value(s)/range(s) that can be used to assess internal bleeding within the patient 202 and can cause an alarm to trigger, such as based on the presence of and/or change in internal bleeding within the patient 202.

Figure 3:
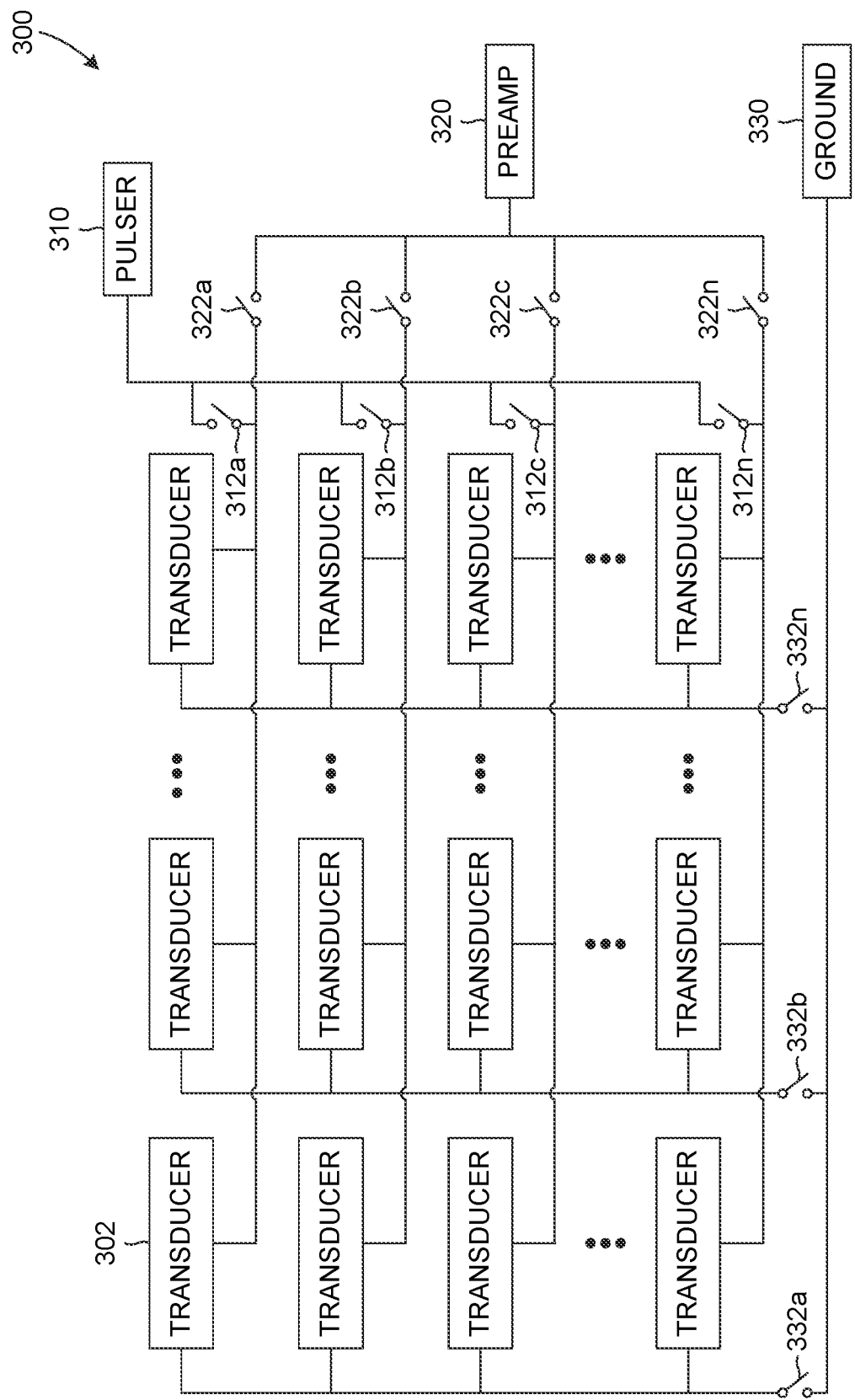
FIG. 3 is an example transducer arrangement.

FIG. 3 is an example transducer arrangement 300 that includes multiple transducers 302 that are coupled to a pulser 310, preamp 320 and ground 330. The transducers 302 are coupled to the pulser 310 by switches 312a-312n, coupled to the preamp 320 by switches 322a-322n and coupled to ground by switches 332a-332n. The coordinated opening and closing of the switches 312a-312n and 322a-322n, and the switches 332a-332n allow for a selected transducer(s) 302 to be activated to emit ultrasound energy and/or receive reflected ultrasound energy. The switches 312a-312n, 322a-322n and 332a-332n control the emission and/or reception of ultrasound energy, and the processing module can control the switches 312a-312n, 322a-322n and 332a-332n.

The transducers 302 are energy emission and reception elements. The transducers 302 generate/emit ultrasound energy when stimulated by an electrical signal, such as by the pulser(s) 310 and generate a voltage/signal in response to receiving energy, such as reflected ultrasound energy. The transducers 302 can be cycled between emission and reception, such as by the switches 312a-312n and 322a-322n, and 332a-332n to radiate ultrasound energy and receive reflected ultrasound energy, such as into and from tissues of a patient.

The pulser(s) 310 can output a signal that is transmitted to connected transducers 302 to cause them to emit ultrasound energy. The ultrasound energy emitted by the connected transducers 302 has characteristics/properties, such as a waveform, power, frequency, wavelength and/or amplitude, based on the signal output by the pulser 310. The connected transducers 302 can be disconnected from the pulser(s) 310 and connected to the preamp(s) 320 to receive reflected ultrasound energy. Alternatively, or additionally, transducers 302 not connected initially to the pulser(s) 310 can be connected to the preamp(s) 320 to receive reflected ultrasound energy. The preamp(s) 320 can also be connected to an analog-to-digital converter(s) to digitize the output of the transducers 302. The ground 330 can be connected to the emitting and/or receiving transducers 302 to complete the circuit and allow the transducers 302 to emit and/or receive ultrasound energy. Although not depicted, currents travel to/from the ground 330 and pulser 310 and preamp 320 to complete the circuit.

The configuration of the system could have a single pulser and single preamp and ADC combination. Other alternative designs could have two pulsers and two preamps and ADCs or any suitable number of corresponding multiple pulsers and preamps and ADC combinations.

In the arrangement shown in FIG. 3, the transducers 302 are connectable, as columns, to the ground 330 by the switches 332a-332n, and connectable, as rows, to the pulser 310 or preamp 320 by the switches 312a-312n or 322a-322n. Coordination of the switches 332a-332n and the switches 312a-312n and/or 322a-322n, can allow individual transducers 302, or a column(s) of transducers 302, to be activated to emit and/or can allow individual transducers 302, or a row(s) of transducers 302 to be activated to receive ultrasound energy.

In an example, all of the transducers 302 can be pulsed by a single transmission from the pulser 310 by closing the switches 312a-312n and 332a-332n. The example pulse can be in the form of a plane wave of ultrasound energy that is transmitted into tissues of the patient. Reflected energy can then be received by/acquired from each transducer 302 individually by cycling the switches 332a-332n and 322a-322n so that each transducer 302 is individually connected to the ground 330 and preamp 320. Alternatively, groupings of transducers 302 can be sampled together by closing desired switched 332a-332n and 322a-322n to define a block of transducers 302 that are then connected to the preamp 320.

The reflected energy received by the transducers 302 generates a reflected energy signal that is output by the transducer arrangement 300. The reflected energy signal can be processed to detect, assess and/or monitor internal bleeding within a patient. Various tissue reflectivities can be determined/assessed from the reflected energy signal to detect/monitor internal bleeding.

Figure 4:
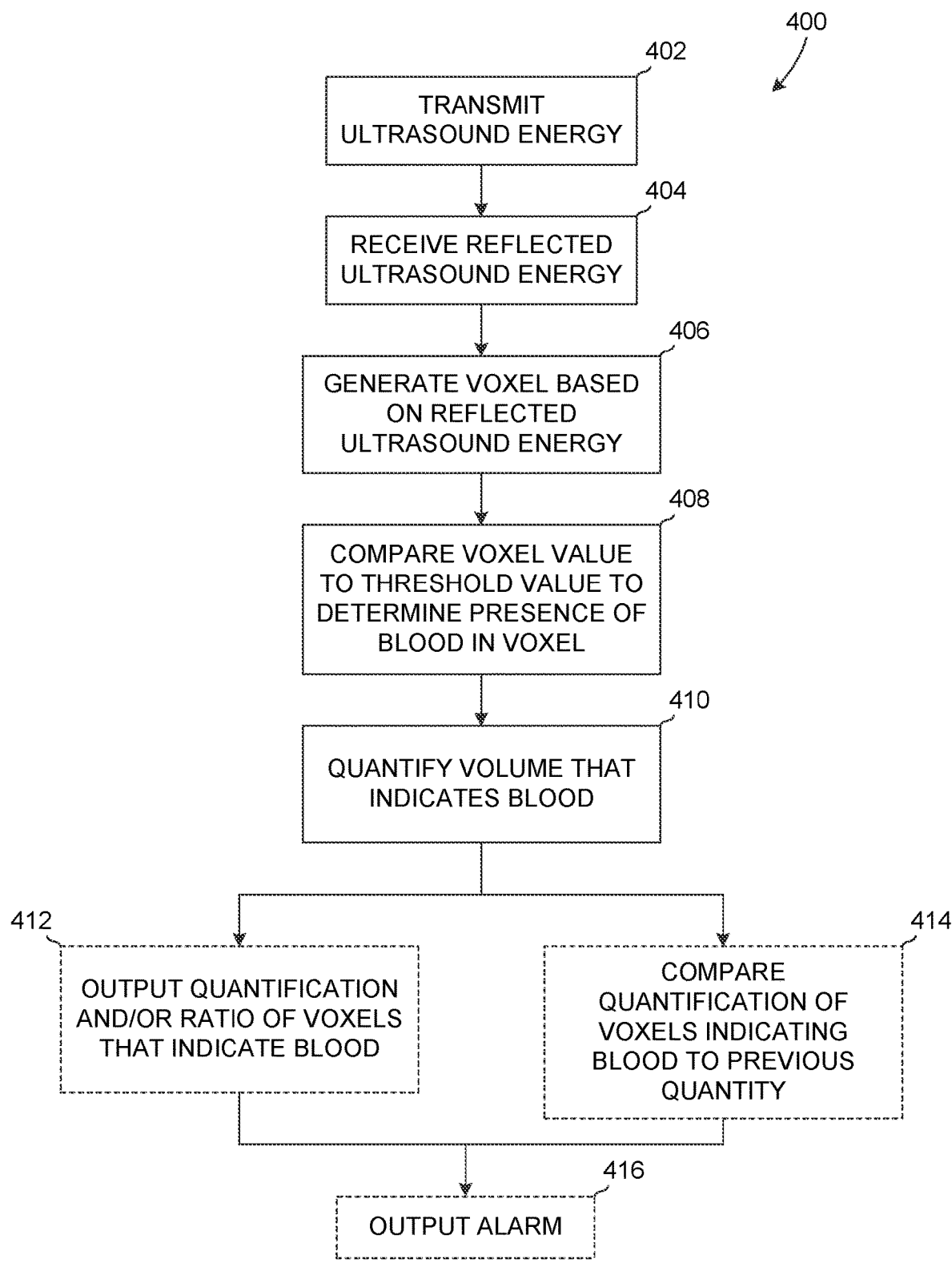
FIG. 4 is an example process for detecting, assessing and/or monitoring internal bleeding.

FIG. 4 is an example process 400 for detecting and/or monitoring internal bleeding. At 402, ultrasound energy is transmitted into the tissues of a patient and at 404 reflected ultrasound energy is received. The transmitted ultrasound energy is transmitted through the tissues of the patient and is, or a portion of it is, reflected from the tissues based on the reflectivity of the tissues/medium. Low reflectivity tissues/mediums, such as blood, reflect less energy than high reflectivity tissues, such as bone. Reflectivity of tissue is due to an impedance change that corresponds to a change in the density and/or speed of sound of the tissue.

At 406, a voxel is generated based on the reflected ultrasound energy. The voxel is a three-dimensional, volumetric pixel representing the volume of tissue interrogated by the ultrasound energy, or the volume of tissue from which the ultrasound energy is primarily reflected. A volume of interest is interrogated by the ultrasound energy and multiple voxels, representing sub-volumes of the volume of interest, are generated from the reflected ultrasound energy.

At 408, a voxel value, such as a power level of the voxel, is compared to a threshold value to determine the presence of blood in the voxel. As discussed above, a power level of each of the voxels may be assessed to determine whether it is above or below a threshold value and/or within or outside of a range of threshold values. Free, or pooled, blood within tissues, that might be caused by internal bleeding, is less reflective than many of the tissues that would be around the free blood. Due to the lower reflectivity of the free blood, compared to the reflectivity of the surrounding tissues, the free blood reflects less ultrasound energy, which results in a reflected energy signal of lower power relative to the reflected energy signal from more reflective tissues. A detection algorithm can compare the power level of each voxel to a threshold value(s) to determine the presence of free blood within the volume of tissue represented by the voxel. The threshold value can be a predetermined, calculated, adjusted and/or input value for the power level of the voxel, below which the voxel can be classified as containing blood.

The detection algorithm can calculate the number of voxels, as discussed above, by determining the number of voxels that do not exceed, or are within, the threshold value(s), for example, and/or by determining a ratio of the voxels that indicate the presence of free blood compared to those that do not exceed the threshold value(s), to the voxels that do not indicate the presence of free blood. The algorithm can use the quantification of the voxels indicating the presence of blood with the volumetric measurement of each of the voxels to provide a measurement (quantification) of the volume of free blood within the volume of interest.

At 410, the voxels that do not exceed the threshold value, such as having a power level less than a predetermined, calculated, adjusted and/or input value, can be quantified, or counted. Each voxel represents a voxel volume in a coordinate system so a volume that exceeds the threshold value can be calculated based on the quantification of the voxels and the volume(s) associated therewith. For example, in the Cartesian coordinate system, the quantification or number of voxels is proportionate to the volume of blood that indicates bleeding. If another coordinate system(s) is used, the quantification of the voxels may have a different relationship to the volume of blood and would then be factored in to determine the quantification of the volume of blood indicating internal bleeding.

At 412, optionally, the quantification, or volume, of voxels that indicate blood can be output. Additionally, or alternatively, a ratio of voxels, or volume of voxels, that indicate blood to the overall voxels/volume, or voxels/volume that do not indicate blood can be output. Based on this output, an alarm or other output indicator can also be optionally output at 416. The alarm can be communicated to a user, device and/or system to cause an action, such as treatment and/or monitoring of the patient, to occur.

At 414, optionally, the quantification of voxels, or volume, that indicate blood can be compared to a previous quantification, or volume. Using this comparison, a change in internal bleeding can be assessed, which can optionally cause an alarm or other output indicator to be output at 416. Additionally, this comparison allows a rate of change to be determined/calculated, with the rate of change being indicative of the rate of change of internal bleeding within the patient.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be used for realizing the invention in diverse forms thereof.

The invention claimed is:

1. An internal bleeding detection device, comprising:
an emitter configured to emit ultrasound into a volume of a patient, the volume comprising at least one of a perihepatic space, a perisplenic space, a pericardium, or a pelvis of the patient;
a sensor configured to detect a first reflection of the ultrasound from the volume at a first time and to detect a second reflection of the ultrasound from the volume at a second time; and
a processor configured to:
generate, by analyzing the first reflection of the ultrasound, first voxels corresponding to respective sections of the volume at the first time;
determine, by analyzing the first voxels at the first time, that a first amount of free blood in the volume of the patient at the first time is less than a threshold amount by determining that less than a threshold number of the first voxels correspond to power levels that are less than a threshold power level;
generate, by analyzing the second reflection of the ultrasound, second voxels corresponding to the respective sections of the volume at the second time;
determine, by analyzing the second voxels at the second time after the first time, that a second amount of free blood in the volume of the patient at the second time is greater than the threshold amount by determining that greater than a threshold number of the second voxels correspond to power levels that are less than the threshold power level; and
in response to determining that the second amount of free blood in the volume of the patient at the second time is greater than the threshold amount, output an alert indicating internal bleeding in the volume.

2. The internal bleeding detection device of claim 1, further comprising:
a pulser electrically coupled to the emitter and being configured to control a characteristic of the ultrasound by supplying energy to the emitter, the characteristic of the ultrasound comprising at least one of a waveform, a power, a frequency, a wavelength, or an amplitude.

3. The internal bleeding detection device of claim 1, wherein the processor is further configured to:
determine, by analyzing the first voxels and the second voxels, a rate of change of the internal bleeding within the patient, and
wherein the processor is configured to output the alert indicating the internal bleeding in the volume further in response to determining that the rate of change of the internal bleeding is greater than a threshold rate of change.

4. A medical device, comprising:
an emitter configured to emit ultrasound into a volume of a patient;
a sensor configured to detect a reflection of the ultrasound from the volume; and
a processor configured to:
generate, by analyzing the reflection of the ultrasound from the volume, voxels corresponding to respective sections of the volume;
determine a number of voxels that have power levels below a threshold power level;
determine that the number of voxels that have power levels below the threshold power level is greater than a threshold number; and
in response to determining that the number of voxels that have power levels below the threshold power level is greater than the threshold number, output an alert indicating internal bleeding in the volume.

5. The medical device of claim 4, further comprising:
a pulser electrically coupled to the emitter and configured to supply energy to the emitter,
wherein a characteristic of the ultrasound emitted by the emitter is dependent on the energy, the characteristic comprising at least one of a waveform, a power, a frequency, a wavelength, or an amplitude.

6. The medical device of claim 4, further comprising:
a pulser electrically coupled to the emitter and configured to supply first energy to the emitter at a first time and second energy to the emitter at a second time, the first energy causing the emitter to emit the ultrasound at a first power level at the first time, the second energy causing the emitter to emit the ultrasound at a second power level at the second time,
wherein the processor is configured to generate the voxels by:
  generating, by analyzing a reflection of the ultrasound at the first power level, a first portion of the voxels corresponding to a first portion of the sections, the first portion of the sections being at a first depth from the emitter; and
  generating, by analyzing a reflection of the ultrasound at the second power level, a second portion of the voxels corresponding to a second portion of the sections, the second portion of the sections being at a second depth from the emitter, the second depth being different than the first depth.

7. The medical device of claim 4, further comprising:
a transmitter configured to transmit, to an external device, an indication of the alert.

8. The medical device of claim 4, wherein the processor is further configured to:
  determine that a first voxel of the voxels is associated with a first power level;
  determine that a second voxel of the voxels is associated with a second power level; and
  map, based on a difference between the first power level and the second power level, a fluid within the volume.

9. The medical device of claim 4, wherein the threshold power level is associated with a power level of free blood.

10. The medical device of claim 4, wherein the threshold power level is lower than a power level associated with a tissue of the patient.

11. The medical device of claim 4, the threshold number being a first threshold number, the alert is a first alert, the processor being further configured to:
  determine that greater than a second threshold number of the voxels are associated with power levels that are below the threshold power level,
  wherein the alert further indicates that the internal bleeding is associated with a severity associated with the second threshold number.

12. The medical device of claim 4, the processor being further configured to:
  determine a ratio of the number of the voxels associated with power levels that are below the threshold power level and a number of the voxels associated with power levels that are above the threshold power level; and
  output, to a user a visual or audible signal indicative of the ratio.

13. A method performed by a medical device, the method comprising:
  emitting, by an emitter, ultrasound into a volume of a patient;
  detecting, by a sensor, a reflection of the ultrasound from the volume;
  generating, by a processor, voxels corresponding to respective sections of the volume;
  determining a number of voxels that have power levels below a threshold power level;
  determining, by the processor, that the number of voxels that have power levels below a threshold power level is greater than a threshold number; and
  in response to determining that the number of voxels that have power levels below the threshold power level is greater than the threshold number, outputting an alert indicating internal bleeding in the volume.

14. The method of claim 13, further comprising:
  supplying energy to the emitter by a pulser electrically coupled to the emitter, wherein a characteristic of the ultrasound emitted by the emitter is dependent on the energy, the characteristic comprising at least one of a waveform, a power, a frequency, a wavelength, or an amplitude.

15. The method of claim 14, wherein the pulser is configured to supply first energy to the emitter at a first time and second energy to the emitter at the second time, the first energy causing the emitter to emit the ultrasound at a first power level at the first time, the second energy causing the emitter to emit the ultrasound at a second power level at the second time, the method further comprising:
  generating, by analyzing a reflection of the ultrasound at the first power level, a first portion of the voxels corresponding to a first portion of the sections, the first portion of the sections being at a first depth from the emitter; and
  generating, by analyzing a reflection of the ultrasound at the second power level, a second portion of the voxels corresponding to a second portion of the sections, the second portion of the sections being at a second depth from the emitter, the second depth being different than the first depth.

16. The method of claim 13, further comprising:
  determining that a first voxel of the voxels is associated with a first power level;
  determining that a second voxel of the voxels is associated with a second power level;
  determining a difference between the first power level and the second power level; and
  mapping, based on the difference between the first power level and the second power level, a fluid within the volume.

17. The method of claim 13, wherein the threshold power level is associated with a power level of free blood.

18. The method of claim 13, wherein the threshold power level is lower than a power level associated with a tissue of the patient.

19. The method of claim 13, the threshold number being a first threshold number, the alert is a first alert, the method further comprising:
  determining that greater than a second threshold number of the voxels are associated with power levels that are below the threshold power level,
  wherein the alert further indicates that the internal bleeding is associated with a severity associated with the second threshold number.

20. The method of claim 13, the method further comprising:
- determining a ratio of the number of the voxels associated with power levels that are below the threshold power level and a number of the voxels associated with power levels that are above the threshold power level; and
- outputting to a user a visual or audible signal indicative of the ratio.

* * * * *